United States Patent
Song et al.

(10) Patent No.: US 12,138,035 B2
(45) Date of Patent: *Nov. 12, 2024

(54) METHOD FOR COUNTING COUGHS BY ANALYZING SOUND SIGNAL, SERVER PERFORMING SAME, AND NON-TRANSITORY COMPUTER-READABLE RECORDING MEDIUM

(71) Applicant: Soundable Heath Korea, Inc., Seoul (KR)

(72) Inventors: Jee Young Song, Seoul (KR); Ji Young Jung, Yongin-si (KR); Sang Youn Kang, Seoul (KR); Kyeong Yeon Doo, Seoul (KR); On Sub Kim, Seoul (KR); Ah Ra Lee, San Jose, CA (US)

(73) Assignee: Soundable Health Korea, Inc., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/544,814

(22) Filed: Dec. 19, 2023

(65) Prior Publication Data

US 2024/0115158 A1    Apr. 11, 2024

Related U.S. Application Data

(63) Continuation of application No. 17/987,104, filed on Nov. 15, 2022, now Pat. No. 11,877,841, which is a
(Continued)

(30) Foreign Application Priority Data

Jul. 13, 2020   (KR) .................. 10-2020-0086464

(51) Int. Cl.
*A61B 5/08*    (2006.01)
*A61B 5/00*    (2006.01)
(Continued)

(52) U.S. Cl.
CPC .......... *A61B 5/0823* (2013.01); *A61B 5/6898* (2013.01); *A61B 5/7203* (2013.01);
(Continued)

(58) Field of Classification Search
None
See application file for complete search history.

(56) References Cited

U.S. PATENT DOCUMENTS

| | | | | |
|---|---|---|---|---|
| 6,168,568 B1 * | 1/2001 | Gavriely | ................ | A61B 5/087 |
| | | | | 600/529 |
| 6,436,057 B1 * | 8/2002 | Goldsmith | ........... | A61B 5/0823 |
| | | | | 600/529 |

(Continued)

FOREIGN PATENT DOCUMENTS

| | | |
|---|---|---|
| KR | 101122590 B1 | 3/2012 |
| KR | 1020140142330 A | 12/2014 |

OTHER PUBLICATIONS

Richard D. Turner, et al., "How to count coughs? Counting by ear, the effect of visual data and the evaluation of anautomated cough monitor," Journal of Respiratory Medicine, Dec. 2014, vol. 108, No. 12, pp. 1808-1815.

(Continued)

*Primary Examiner* — Michael R Bloch
(74) *Attorney, Agent, or Firm* — Dinsmore & Shobl LLP; Yongsok Choi, Esq.

(57) ABSTRACT

A method for counting coughs is provided. The method includes acquiring a plurality of onset signals from the sound signal, wherein the onset signal has a predetermined time length; acquiring a plurality of spectrograms corresponding to each of the plurality of onset signals; determining whether each of the acquired plurality of spectrograms represents a cough using a cough determination model; and calculating a number of coughs included in the sound signal based on a time point of a cough signal. The cough signal is an onset signal corresponding to one spectrogram determined to represent the cough. When a time interval between a first time point of a first cough signal and a second time point of a second cough is within a reference time interval, the first cough signal and the second cough signal are regarded as one cough signal at the first time point.

12 Claims, 7 Drawing Sheets

Related U.S. Application Data continuation of application No. PCT/KR2021/008956, filed on Jul. 13, 2021.

(51) Int. Cl.
  *A61B 7/00*    (2006.01)
  *G16H 30/40*   (2018.01)
(52) U.S. Cl.
  CPC ............ *A61B 5/7267* (2013.01); *A61B 7/003* (2013.01); *G16H 30/40* (2018.01)

(56)           References Cited

U.S. PATENT DOCUMENTS

2012/0071777 A1     3/2012  Macauslan
2014/0336537 A1*   11/2014  Patel .................... A61B 5/0816
                                                        600/586
2015/0073306 A1*    3/2015  Abeyratne ............. G16H 50/30
                                                        600/586
2020/0015709 A1     1/2020  Peltonen et al.
2021/0319804 A1    10/2021  Whitehill et al.

OTHER PUBLICATIONS

Written Opinion of the International Search Authority of PCT/KR2021/008956 dated Oct. 19, 2021.
International Search Report of PCT/KR2021/008956 dated Oct. 19, 2021.

* cited by examiner

| TIME POINT (hour:minute:sec) | TAG |
|---|---|
| 00:00:15.5 | COUGH |
| 00:00:15.7 | COUGH |
| 00:15:00 | NON-COUGH |
| 00:17:20 | COUGH |
| 00:17:20.5 | COUGH |
| 00:22:00 | COUGH |

00:00:15.5, 00:00:15.7 → COUNT ONE

00:17:20, 00:17:20.5 → COUNT TWO

METHOD FOR COUNTING COUGHS BY ANALYZING SOUND SIGNAL, SERVER PERFORMING SAME, AND NON-TRANSITORY COMPUTER-READABLE RECORDING MEDIUM

CROSS-REFERENCE TO RELATED APPLICATIONS

This application is a continuation of U.S. patent application Ser. No. 17/987,104 filed on Nov. 15, 2022, which is a continuation of International Application No. PCT/KR2021/008956 filed on Jul. 13, 2021, which claims priority to Korean Patent Application No. 10-2020-0086464 filed on Jul. 13, 2020, the entire contents of which are herein incorporated by reference.

TECHNICAL FIELD

Embodiments relate to a method for counting coughs based on a sound signal, a server for performing the method, and a non-transitory computer-readable recording medium.

BACKGROUND ART

The number of coughs is the most basic and important indicator for assessing the degree of coughing objectively, but the only way to count coughs is by an expert listening to cough sounds and counting coughs in person.

Specifically, due to the nature of respiratory diseases that require continuous management, a quantitative monitoring platform is needed in addition to a cough analysis through 24-hour recording at a hospital. However, currently, 1) a patient visits a medical institution and a questionnaire/a medical examination by interview is conducted about the frequency of coughs, intensity, and disruption in life due to coughing based on a patient's subjective feelings and memory in order to diagnose severity and give a medical treatment, or 2) in the course of hospital treatment and clinical trials of global pharmaceutical companies, to assess the degree of coughing, a recorder is attached to a patient to record a sound for several tens of minutes to 24 hours and an expert listens to the recording file to count the number of coughs. All patients/medical workers lack medical information with objectivity and efficiency secured.

A method of visualizing waveforms of a recording file for counting has been proposed, but also in this method, a person looks at the waveforms and counts the number of coughs in person, which does not solve the basic problem of objectivity and efficiency ("How to count coughs? Counting by ear, the effect of visual data and the evaluation of an automated cough monitor," R. D. Turner and G. H. Bothamley, Respiratory Medicine, December 2014 hpps://www-.sciencedirect.com/science/article/pii/S0954611114003357).

Accordingly, there is a need to develop a method for counting coughs accurately based on a sound signal.

SUMMARY

Technical Problem

An embodiment is directed to providing a method for counting coughs accurately based on a sound signal.

Technical Solution

According to one embodiment of the present specification, a method for counting coughs by analyzing a sound signal may be provided, the method comprises: acquiring a plurality of onset signals from the sound signal, wherein the onset signal has a predetermined time length from an onset point included in the sound signal; acquiring a plurality of spectrograms corresponding to each of the plurality of onset signals; determining whether each of the acquired plurality of spectrograms represents a cough using a cough determination model; and calculating a number of coughs included in the sound signal based on a time point of a cough signal, wherein the cough signal is an onset signal corresponding to one spectrogram determined to represent the cough, wherein when a time interval between a first time point of a first cough signal and a second time point of a second cough signal later than the first cough signal is within a reference time interval, the first cough signal and the second cough signal are regarded as one cough signal at the first time point.

According to another embodiment of the present specification, a server for counting coughs by analyzing a sound signal may be provided, the server comprises: a communication part configured to acquire the sound signal comprising a sound recorded from an external device; a memory configured to store instructions for loading a cough determination model; and a controller configured to execute the instructions to: acquire a plurality of onset signals from the sound signal, wherein the onset signal has a predetermined time length from an onset point included in the sound signal, acquire a plurality of spectrograms corresponding to each of the plurality of onset signals, determine whether each of the acquired plurality of spectrograms represents a cough using a cough determination model, and calculate a number of coughs included in the sound signal based on a time point of a cough signal, wherein the cough signal is an onset signal corresponding to one spectrogram determined to represent the cough, wherein when a time interval between a first time point of a first cough signal and a second time point of a second cough signal later than the first cough signal is within a reference time interval, the first cough signal and the second cough signal are regarded as one cough signal at the first time point.

Advantageous Effects

According to the embodiment, provided is a method for counting coughs accurately while reducing the amount of operation to be processed, in counting coughs based on a sound signal.

The present application is not limited to the above-mentioned effects. From the present specification and the accompanying drawings, an effect not mentioned above would be understandable to a person of ordinary skill in the art to which the present application pertains.

DETAILED DESCRIPTION

The above-described objectives, features, and advantages of the present application will be more apparent from the following detailed description with reference to the accompanying drawings. In addition, various modifications may be made to the present application, and various embodiments of the present application may be practiced. Therefore, specific embodiments will be described in detail below with reference to the accompanying drawings.

In the drawings, the thickness of layers and regions are exaggerated for clarity. In addition, when an element or a layer is referred to as being "on" another element or layer, it may be directly on the other element or layer or an intervening layer or element may be present therebetween. Throughout the specification, the same reference numerals denote the same elements in principle. In addition, elements having the same function within the same scope illustrated in the drawings of the embodiments are described using the same reference numerals.

A detailed description of a well-known function or configuration relating to the present application is omitted when determined as obfuscating the nature and gist of the present application. In addition, throughout the present specification, the terms first, second, and so on are used only to distinguish from one element to another.

In addition, the terms "module" and "part" that are used to name an element in the description below are used considering only the ease with which the present specification is written. The terms are not intended as having different special meanings or functions and thus may be used individually or interchangeably.

According to an embodiment of the present specification, a method for counting coughs by analyzing a sound signal may be provided, and the method may include acquiring a plurality of onset signals from the sound signal, wherein the onset signal may have a predetermined time length from an onset point included in the sound signal; acquiring a plurality of spectrograms corresponding to each of the plurality of onset signals; determining whether each of the acquired plurality of spectrograms represents a cough using a cough determination model; and calculating a number of coughs included in the sound signal based on a time point of a cough signal, wherein the cough signal may be an onset signal corresponding to one spectrogram determined to represent the cough, wherein when a time interval between a first time point of a first cough signal and a second time point of a second cough signal later than the first cough signal is within a reference time interval, the first cough signal and the second cough signal may be regarded as one cough signal at the first time point.

There may be no cough signal between the first cough signal and the second cough signal.

The calculating the number of coughs may include comparing sequentially the time points of the cough signals, and determining the number of coughs included in the sound signal, wherein, in response to regarding the first cough signal and the second cough signal as the one cough signal by comparing the first time point and the second time point, consecutively a third time point of a third cough signal later than the second cough signal and a fourth time point of a fourth cough signal later than the third cough signal may be compared.

There may be no cough signal between the first cough signal and the second cough signal, and there may be no cough signal between the second cough signal and the third cough signal.

The predetermined time length may be longer than the reference time interval.

The calculating the number of coughs may include determining whether the time interval between the first time point and the second time point is within the reference time interval.

The time point may be determined based on a time value of the onset point corresponding to the cough signal.

The acquiring the plurality of onset signals may include detecting the onset point in the sound signal; and extracting a signal corresponding to the predetermined time length from the detected onset point.

The acquiring the plurality of spectrograms may include acquiring the plurality of spectrograms by Fourier transforming each of the acquired plurality of onset signals in the frequency domain.

The acquiring the plurality of spectrograms may include extracting a spectrogram corresponding to the acquired onset signal from a total spectrogram acquired by transforming the sound signal into a frequency domain.

The determining whether each of the acquired plurality of spectrograms represents the cough may include performing at least one preprocessing of resizing, scaling and RGB conversion on the acquired spectrogram; and determining whether the spectrogram represents the cough by inputting the preprocessed spectrogram into the cough determination model.

The cough determination model may be a classification model trained to classify inputted spectrogram data into a cough or non-cough, wherein the spectrogram data may be a spectrogram image having the predetermined time length in a time domain.

The cough determination model may be trained using a training dataset comprising a plurality of the spectrogram data and tagging information labeled on each of the plurality of the spectrogram data, wherein the tagging information may include information on whether the spectrogram data represents a sound corresponding to a cough.

According to another embodiment of the present specification, a non-transitory computer-readable recording medium storing a computer program for executing the method for counting coughs by analyzing a sound signal may be provided.

According to another embodiment of the present specification, a server for counting coughs by analyzing a sound signal may be provided, and the server may include a communication part configured to acquire the sound signal comprising a sound recorded from an external device; a memory configured to store instructions for loading a cough determination model; and a controller configured to execute the instructions to acquire a plurality of onset signals from the sound signal, wherein the onset signal may have a predetermined time length from an onset point included in the sound signal, acquire a plurality of spectrograms corresponding to each of the plurality of onset signals, determine whether each of the acquired plurality of spectrograms represents a cough using a cough determination model, and calculate a number of coughs included in the sound signal based on a time point of a cough signal, wherein the cough signal may be an onset signal corresponding to one spectrogram determined to represent the cough, wherein when a time interval between a first time point of a first cough signal and a second time point of a second cough signal later than the first cough signal is within a reference time interval, the first cough signal and the second cough signal may be regarded as one cough signal at the first time point.

The controller may configured to compare sequentially the time points of the cough signals, and determine the number of coughs included in the sound signal, wherein, in response to regarding the first cough signal and the second cough signal as the one cough signal by comparing the first time point and the second time point, consecutively a third time point of a third cough signal later than the second cough signal and a fourth time point of a fourth cough signal later than the third cough signal may be compared.

There may be no cough signal between the first cough signal and the second cough signal, and there may be no cough signal between the second cough signal and the third cough signal.

The predetermined time length may be longer than the reference time interval.

The controller may be configured to determine whether the time interval between the first time point and the second time point is within the reference time interval.

The controller may be configured to detect the onset point in the sound signal; and extract a signal corresponding to the predetermined time length from the detected onset point.

Figure 1:
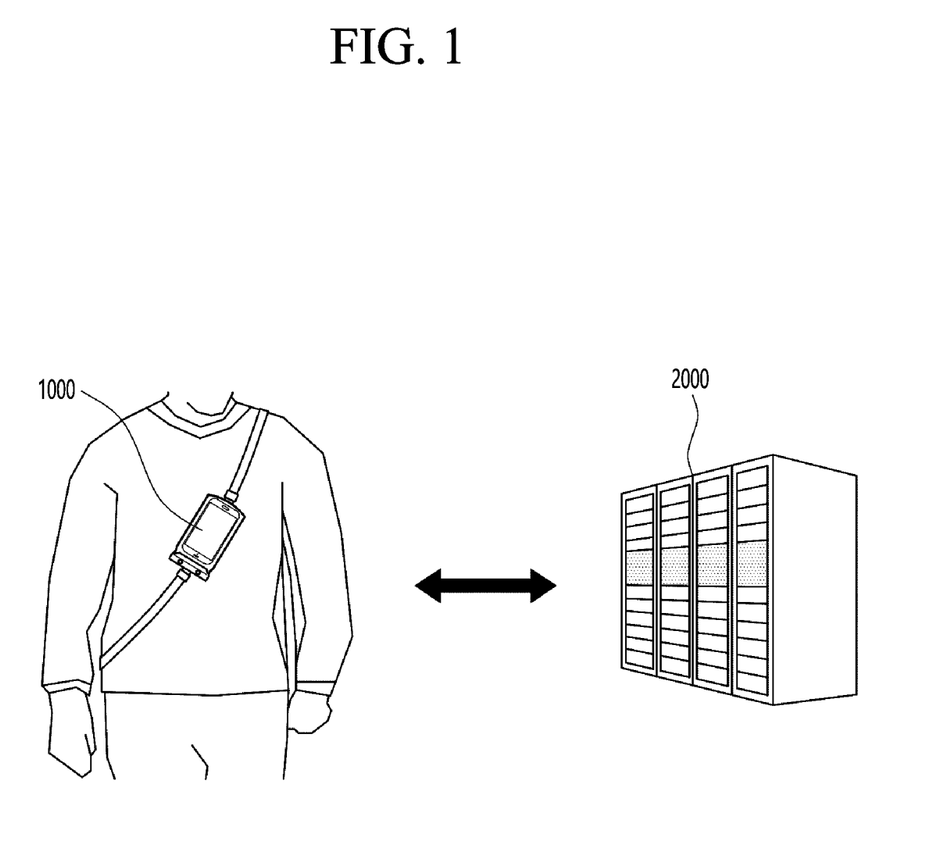
FIG. 1 is a view schematically showing a configuration of the entire system 10 for counting coughs according to an embodiment of the present application.

FIG. 1 is a view schematically showing a configuration of the entire system 10 for counting coughs according to an embodiment of the present application.

According to the embodiment of the present application, the system 10 may include a device 1000 and a server 2000. However, the elements shown in FIG. 1 are not essential, and the system 10 may include more elements or fewer elements.

The device 1000 may be connected to the server 2000 over a network, and may transmit/receive necessary data. Herein, the network may include a local area network (LAN), a metropolitan area network (MAN), a wide area network (WAN), Wi-Fi, Wi-Fi Direct, LTE Direct, and/or Bluetooth, but is not limited thereto.

Fixed to part of a person's body, the device 1000 may perform a function of recording a sound for a determined time period. An input device, such as a microphone, of the device 1000 may obtain and record an external sound for a determined length of time (e.g., 24 hours). A sound signal including the recorded sound may be transmitted to the server 2000 over the network. Herein, with the microphone facing the person's face, the device 1000 may be fixed at the person's abdomen side or on the person's arm. When fixing the device 1000, a commonly used belt, armband, or the like may be used.

The device 1000 is a digital device to which a function of accessing the server 2000 to transmit data is applied. The device 1000 may be a digital device having a memory means and equipped with a micro processor to have an operation ability. For example, the device 1000 may be a wearable device, such as smart glasses, a smart watch, a smart band, a smart ring, or a smart necklace, or may be a somewhat conventional device, such as a smartphone, a smart pad, a desktop computer, a laptop computer, a workstation, a PDA, a web pad, or a mobile phone.

The server 2000 may perform a function of analyzing a sound signal to count coughs. The server 2000 may extract one or more onset signals from the sound signal, and may apply input data obtained on the basis of the extracted onset signals to a cough determination model, thereby calculating the total number of coughs in the sound signal.

According to an embodiment of the present application, the server 2000 extracts one or more onset signals to determine a cough/non-cough, and omits an operation of applying the entire sound signal to the cough determination model, thus dramatically reducing the amount of operation of the server required to determine a cough. In addition, according to an embodiment of the present application, in calculating the total number of coughs, the server 2000 counts one or two on the basis of a time interval between the time points of onset signals determined as two adjacent coughs through a pre-stored algorithm, thus calculating the total number of coughs accurately without a problem that one cough of which a cough sound is recorded long is double-counted.

The functions of the server 2000 will be described below in more detail.

In the meantime, in the present specification, a detailed method for counting coughs is described as being performed by the server 2000, but this description is exemplary. It is apparent to a person skilled in the art that all or some functions described as the operation of the server 2000 in the present specification may be performed by the device 1000.

In addition, in the case in which the device 1000 performs a method for counting coughs described in the present specification, the device 1000 may further include an application program for performing the method. The application may be present in the form of a program module in the device 1000. The characteristics of the program module may be generally similar to those of a communication part 2100, a memory 2200, and a controller 2300, which will be described later. Herein, at least part of the application may be replaced with a hardware device or a firmware device capable of performing the function substantially the same as or equivalent to the at least part when necessary.

Figure 2:
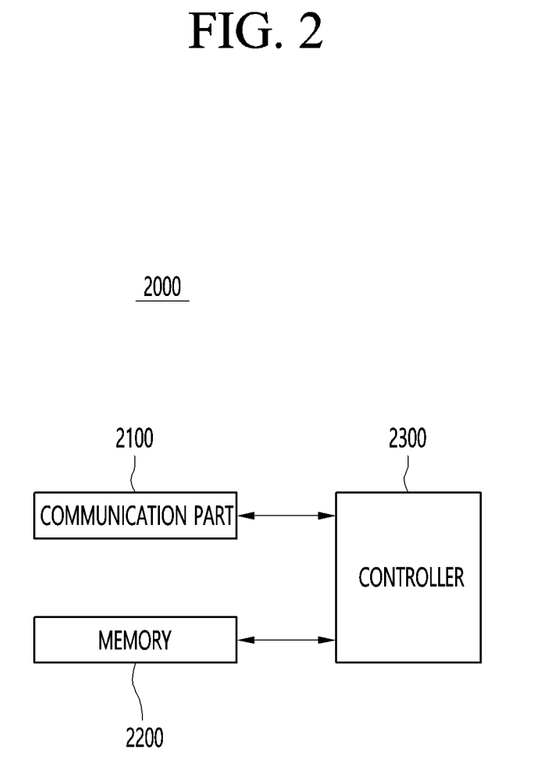
FIG. 2 is a view showing elements of a server 2000 according to an embodiment of the present application.

FIG. 2 is a view showing elements of a server 2000 according to an embodiment of the present application. Referring to FIG. 2, the server 2000 may include a communication part 2100, a memory 2200, and a controller 2300. However, the elements shown in FIG. 2 are not essential, and the server 2000 may include more elements or fewer elements.

According to an embodiment of the present application, the elements of the server 2000 may be physically included in one server, or may be servers distributed by functions, but are not limited thereto.

According to an embodiment of the present application, at least some of the communication part 2100, the memory 2200, and the controller 2300 of the server 2000 may be program modules communicating with an external system (not shown). These program modules may be included in the server 2000 in the form of an operating system, an application program module, and other program modules, and may be physically stored in various known storage devices. In addition, the program modules may be stored in a remote storage device capable of communicating with the server 2000. In the meantime, the program modules include routines, subroutines, programs, objects, components, and data structures that perform particular tasks to be described later or execute particular abstract data types according to the present application, but are not limited thereto.

The communication part 2100 may enable the server 2000 to transmit/receive data to or from an external device (for example, the device 1000).

The communication part 2100 may include one or more modules that enables communication. The communication part 2100 may include a module that enables communication with an external device in a wired manner. Alternatively, the communication part 2100 may include a module that enables communication with an external device in a wireless manner. Alternatively, the communication part 2100 may include a module that enables communication with an external device in a wired manner, and a module that enables communication with an external device in a wireless manner.

As a specific example, the communication part 2100 may be provided as one of the following or a combination thereof: a wired communication module for accessing the Internet over a local area network (LAN); a mobile communication module for accessing a mobile communication network through a mobile communication base station and transmitting and receiving data, for example, Long-Term Evolution (LTE); a short-range communication module using a wireless local area network (WLAN) communication method such as Wi-Fi or using a wireless personal area network (WPAN) communication method such as Bluetooth and Zigbee; and a satellite communication module using a global navigation satellite system (GNSS) such as the Global Positioning System (GPS).

According to an embodiment of the present application, the communication part 2100 may receive a sound signal through the device 1000. According to an embodiment of the present application, the communication part 2100 may analyze a sound signal received from the device 1000, and may transmit the total number of coughs with respect to the sound signal to the device 1000.

The memory 2200 may store therein various types of data and programs required for the server 2000 to operate. For example, the memory 2200 may store therein the following: an operating program (operating system, OS) for driving the server 2000 for counting coughs on the basis of a sound signal; various programs that are required to be run or used in the server 2000 to perform the method for counting coughs; and various types of data of media to be referenced by the programs.

The memory 2200 may store data therein temporarily or semi-permanently. Examples of the memory 2200 include a hard disk drive (HDD), a solid-state drive (SSD), a flash memory 1400, a read-only memory (ROM), a random-access memory (RAM), and a cloud storage. In addition, the memory 2200 may build and store a database for storing data, and without being limited thereto, the memory 2200 may be realized as various modules for storing data.

According to an embodiment of the present application, the memory 2200 may store therein the cough determination model. According to another embodiment of the present application, the memory 2200 may store therein an instruction for loading the cough determination model.

The cough determination model may be provided as a machine learning algorithm, such as a supervised learning algorithm (for example, logistic regression, support-vector machine (SVM), random forest, etc.), an unsupervised learning algorithm, artificial neural networks (ANNs), etc., or may be provided as a deep learning algorithm, such as a fully connected network, a convolutional neural network (CNN), etc. In the meantime, the cough determination model according to an embodiment of the present application is not necessarily limited to those listed above, and may be variously changed within the scope that can achieve the purpose of the present disclosure.

According to an embodiment of the present application, the cough determination model may be a classification model that receives spectrogram data to be trained to output a marker for whether it is a cough period. For example, the cough determination model may be a classification model that receives spectrogram data to be trained to perform classification into a cough or a non-cough. Herein, the spectrogram data may be a spectrogram image having a pre-determined length in the time domain.

According to an embodiment of the present application, the cough determination model may be trained using a training data set including the spectrogram data and tagging information labeled on the spectrogram data. Herein, the tagging information may include information on whether the spectrogram data includes a sound corresponding to a cough. Herein, the tagging information may be a value that is selected on the basis of information previously processed by a medical professional. For example, labeling of whether a sound corresponds to a cough may be determined on the basis of data previously processed by a medical professional.

A process of training the cough determination model according to an embodiment of the present application may be performed by the controller 2300 included in the server 2000 or may be performed by an entity (for example, a training server distinguished from the server 2000) separate from the server 2000.

In addition, the memory 2200 may store therein an onset detection module, an onset signal extraction module, a spectrogram acquisition module (not shown), a data preprocessing module, and/or a cough determination module (including the cough determination model). The modules may be present in the server 2000 as separate modules that are functionally distinguished, or may be present in the server 2000 as a physically integrated module as one subject performs the roles of a plurality of functional modules. The function and the operation of each module will be clearly understood with a method for counting coughs, which will be described below, and thus a detailed description thereof will be omitted.

The controller 2300 may perform a function of managing and controlling the overall operation of the server 2000. The controller 2300 may perform operation and processing of various types of information, and may control the operation of the elements of the server 2000.

The controller 2300 may be realized as a computer or a similar device according to hardware, software, or a combination thereof. In terms of hardware, the controller 2300 may be provided in the form of an electronic circuit, such as a CPU chip, for performing a control function by processing electrical signals. In terms of software, the controller 2300 may be provided in the form of a program for driving a hardware controller.

According to an embodiment of the present application, the controller 2300 may extract one or more onset signals from a sound signal received through the communication part 2100. The controller 2300 may use the onset detection module and the onset signal extraction module to extract one or more onset signals from a sound signal. An onset signal may include a signal corresponding to an attack of a sound, and may have a predetermined length in the time domain.

According to an embodiment of the present application, the controller 2300 may obtain a spectrogram corresponding to the extracted onset signal. The controller 2300 may obtain the spectrogram corresponding to the extracted onset signal by using a spectrogram conversion module. Alternatively, using the spectrogram conversion module, the controller 2300 may obtain the entire spectrogram of a sound signal, may perform cropping for only a part corresponding to an extracted onset signal from the entire spectrogram, and may obtain a spectrogram corresponding to the extracted onset signal.

According to an embodiment of the present application, the controller 2300 may determine whether the obtained spectrogram represents a cough period. The controller 2300 may determine whether there is a cough period by applying input data based on the spectrogram to the cough determination model.

According to an embodiment of the present application, the controller 2300 may calculate the total number of coughs in the sound signal on the basis of a determination result with respect to a spectrogram of an onset signal. Herein, the controller 2300 may perform an operation of obtaining a spectrogram corresponding to an onset signal and determining whether the obtained spectrogram represents a cough period, and the operation is performed as many times as the number of extracted onset signals. In the step of calculating the total number of coughs, the controller 2300 may compare time points of onset signals determined as coughs. When the time point of a first onset signal and the time point of a second onset signal are spaced apart by more than a reference time interval, the controller 2300 counts the onset signals as two. When the time point of the first onset signal and the time point of the second onset signal are spaced apart within the reference time interval, the controller 2300 counts the onset signals as one. Herein, the first onset signal and the second onset signal are signals determined as coughs.

Hereinafter, an operation of counting coughs on the basis of a sound signal will be described in detail. However, hereinafter, unless otherwise specified, the operation of the server 2000 may be interpreted as being performed under the control of the controller 2300.

Figure 3:
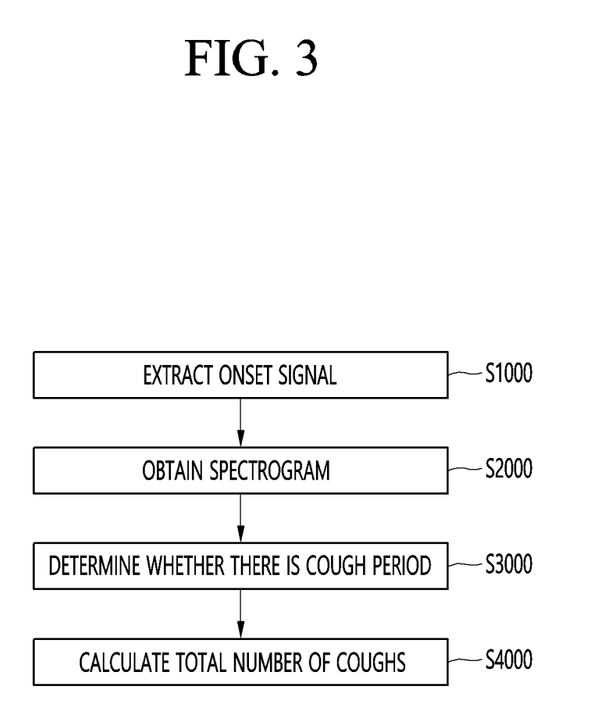
FIG. 3 is a flowchart showing a method for counting coughs according to an embodiment of the present application.

FIG. 3 is a flowchart showing a method for counting coughs according to an embodiment of the present application.

A server 2000 may extract an onset signal in step S1000. The server 2000 may extract the onset signal on the basis of a sound signal received through a communication part 2100. The server 2000 may extract the onset signal from the received sound signal, or may extract the onset signal by performing noise filtering on the received sound signal.

Figure 4:
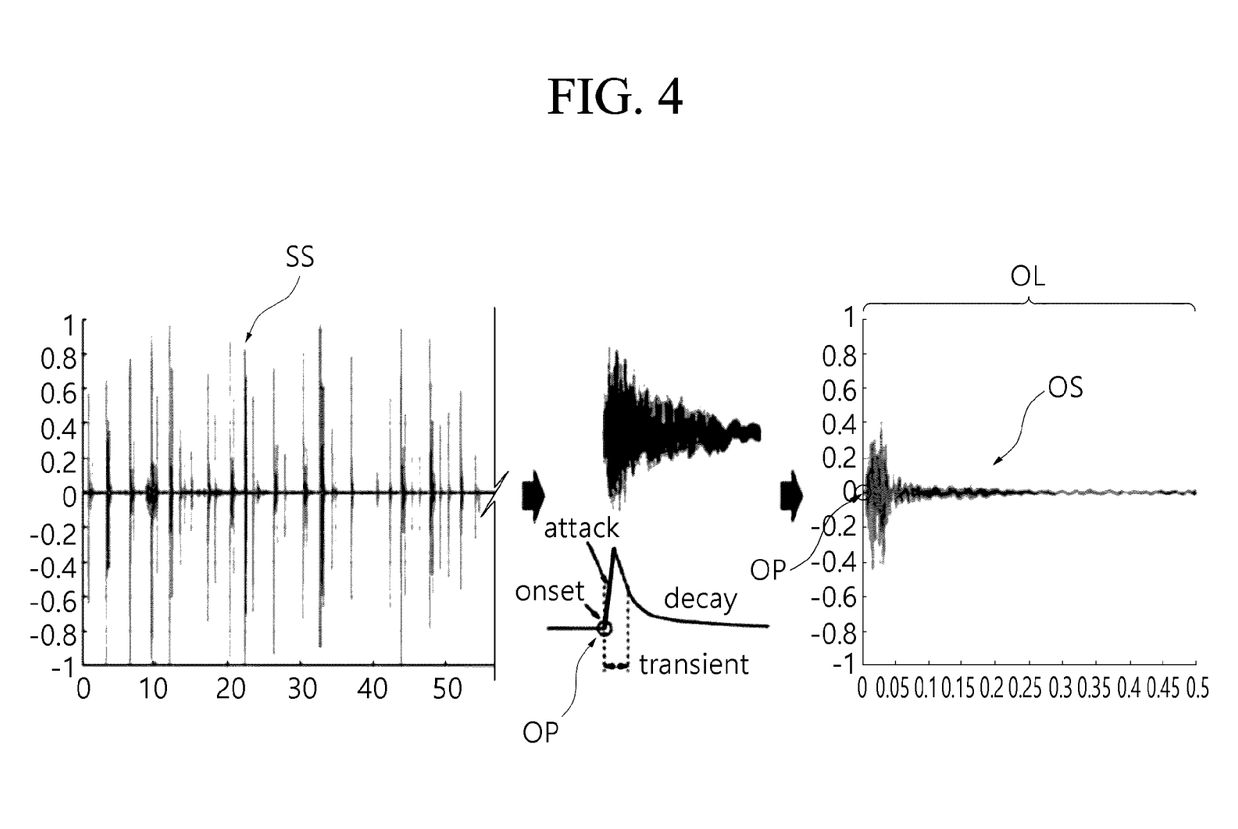
FIG. 4 is a view showing a method of detecting an onset signal according to an embodiment of the present application.

FIG. 4 is a view showing a method of detecting an onset signal according to an embodiment of the present application.

According to the embodiment of the present application, a server 2000 may extract an onset point (OP) from a sound signal (SS).

The server 2000 determines whether there is an onset point (OP) every sampling time (e.g., 0.01 s). When an onset point (OP) is determined, an onset signal (OS) is obtained from the sound signal (SS) by performing cropping for a signal that corresponds to a time span of a pre-determined length of time (onset length, OL) from the time point of the onset point. The onset signal (OS) may include a signal corresponding to an attack of a sound. The onset signal (OS) may have a predetermined length (OL) in the time domain. Herein, the number of onset signals (OSs) obtained may be the same as the number of onset points (OPs) determined.

A method of determining whether there is an onset point (OP) is to select, as the onset point (OP), a point at which an onset intensity obtained every determined sampling time is greater than a reference intensity. As a specific example, regarding the onset intensity, the onset intensity may be obtained on the basis of a mel-spectrogram passed through a mel-filter bank. As a specific example, the controller 2300 may divide the obtained sound signal (SS) into two or more frequency sections, and may add the values obtained by passing each of the divided signals through the mel-filter bank, thereby obtaining an onset intensity. The controller 2300 may determine there is an onset point (OP) when the obtained onset intensity is greater than the reference intensity. The controller 2300 may determine there is an onset point (OP) when the obtained onset intensity is greater than the reference intensity and the onset intensity obtained immediately before is less than the reference intensity. Herein, the reference intensity may be a pre-determined constant value. Alternatively, the reference intensity may be variably defined by referring to an onset intensity in the entire sound signal (SS) or near a point to be determined.

Figure 5:
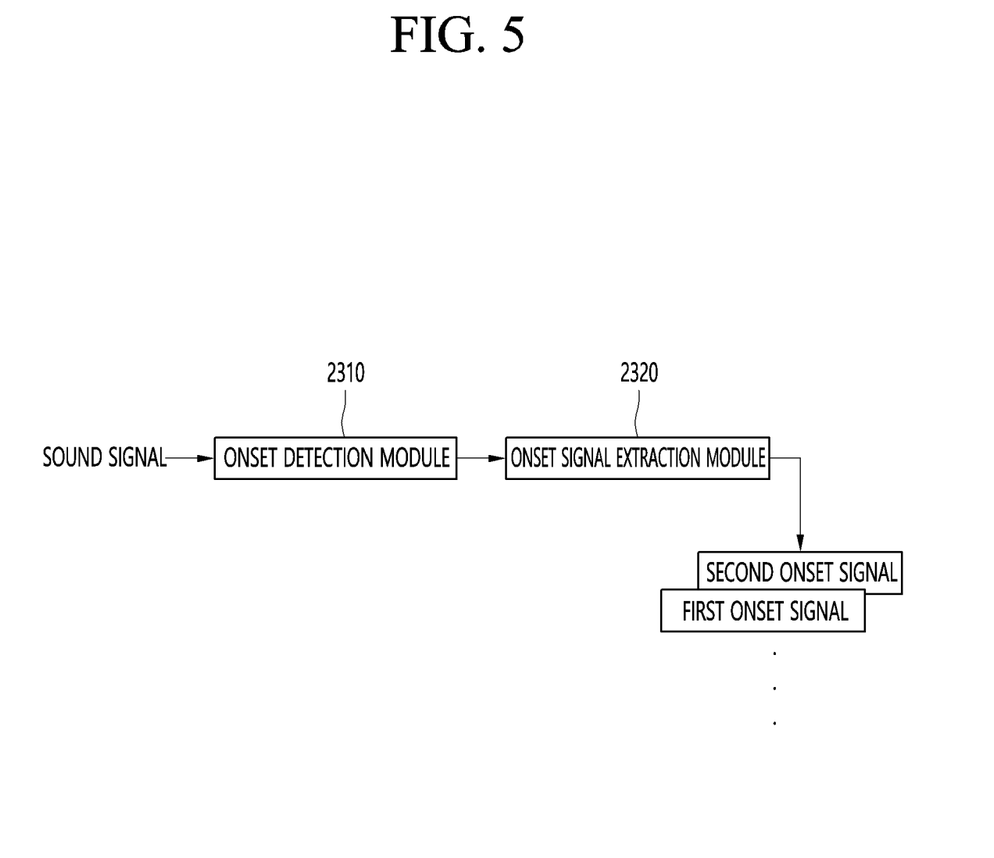
FIG. 5 is a view showing a module, which is included in a controller 2300, for detecting an onset signal, according to an embodiment of the present application.

FIG. 5 is a view showing a module, which is included in a controller 2300, for detecting an onset signal, according to an embodiment of the present application.

According to an embodiment of the present application, an onset detection module 2310 may perform an operation of detecting an onset point on the basis of a sound signal received. The onset detection module 2310 may detect an onset point by scanning the entire sound signal at determined intervals. The onset detection module 2310 may detect an onset point in the sound signal, and a plurality of onset points may be detected.

An onset signal extraction module 2320 may extract an onset signal from the onset point detected by the onset detection module 2310. The onset signal extraction module 2320 may extract an onset signal at every onset point detected. The onset signal extraction module 2320 may extract an onset signal by cropping a signal that corresponds to a pre-determined length of time starting from the detected onset point.

According to an embodiment of the present application, as the onset detection module 2310 and the onset signal extraction module 2320 operate, a first onset signal, a second onset signal, . . . , and an Nth onset signal may be extracted from the sound signal. Herein, a determined interval at which the onset detection module 2310 performs scanning may be shorter than the length of an onset signal. In this case, the first onset signal and the second onset signal may overlap.

Referring back to FIG. 3, the server 2000 may obtain a spectrogram in step S2000.

For example, the server 2000 may obtain a spectrogram on the basis of the extracted onset signal. As another example, the server 2000 may extract a spectrogram corresponding to an onset signal extracted from the entire spectrogram obtained on the basis of a sound signal.

A method of converting a signal having an amplitude value in the time domain into a spectrogram having an amplitude value in the frequency domain may be performed according to a commonly known method. As an example, a signal to be converted may be divided according to a determined time span, the signals resulting from division are decomposed into individual sine waves through fast Fourier transform, and magnitude signals according to the decomposed frequencies are expressed as frequency over time, displaying the amplitude with color, whereby conversion into a spectrogram is performed. Without being limited thereto, the term "spectrogram" in the present application may include all spectrograms having a general meaning. As a specific example, the spectrogram in the present application may be a mel spectrogram in which a frequency is converted to a mel scale.

According to an embodiment of the present application, obtained may be a first spectrogram, a second spectrogram, . . . , and an Nth spectrogram corresponding to a first onset signal, a second onset signal, . . . , an Nth onset signal extracted from the sound signal, respectively. The spectrogram acquisition module may obtain as many spectrograms as there are onset signals obtained by the onset signal extraction module 2320. For example, the spectrogram acquisition module may perform an operation of converting an onset signal into a spectrogram as many times as the number of onset signals obtained by the onset signal extraction module 2320. As another example, the spectrogram acquisition module may perform an operation of converting the sound signal into a full spectrogram, and may perform an operation of extracting a spectrogram corresponding to an onset signal from the entire spectrogram as many times as the number of onset signals obtained by the onset signal extraction module 2320.

The server 2000 may determine whether there is a cough period in step S3000. The server 2000 may determine whether there is a cough period in step S3000 on the basis of the spectrogram obtained in step S2000.

Figure 6:
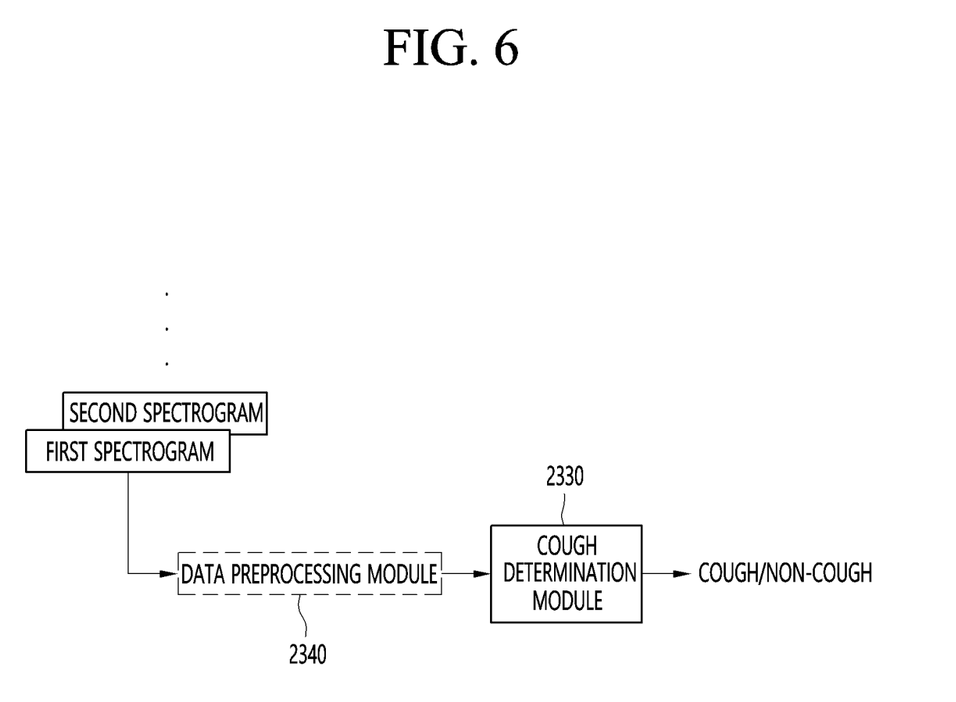
FIG. 6 is a view showing a cough determination operation according to an embodiment of the present application.

FIG. 6 is a view showing a cough determination operation according to an embodiment of the present application.

The cough determination module 2330 may determine whether there is a cough period on the basis of a spectrogram corresponding to an onset signal. The cough determination module 2330 may include the cough determination model that receives spectrogram data to be trained to perform classification into a cough or a non-cough.

The spectrogram data may be a spectrogram having a pre-determined length in the time domain. The spectrogram data may be a spectrogram corresponding to the onset signal extracted in step S1000.

If necessary, a data preprocessing module 2340 may perform preprocessing before the spectrogram data is input to the cough determination module 2330. The spectrogram data may be data that is obtained by performing, by the data preprocessing module 2340, at least one preprocessing among resizing, scaling, and gray-to-RGB conversion on the spectrogram corresponding to the onset signal extracted in step S1000. As a specific example, the data preprocessing module 2340 may resize the spectrogram.

According to an embodiment of the present application, the cough determination model may be trained using a training data set including the spectrogram data and tagging information labeled on the spectrogram data. Herein, the tagging information may include information on whether the spectrogram data represents a sound corresponding to a cough.

In a specific experimental example, the cough determination model was built using EfficientNet.

According to experimental example 1, using Efficient Net B5, a spectrogram having a period of 0.5 s was used as input data, and cough/non-cough markers assessed by a person after listening to a recorded sound were applied as output data. Regarding the input data, one spectrogram was divided by frequency section and the divided spectrogram was input to a total of 512 input nodes separately. Before input to the model, the spectrogram was subjected to resizing to a size of 300*300, scaling with division by a maximum value, and gray-to-RGB conversion. A total of 350,000 pieces of training data were used to train the cough determination model, and the cough determination model showed accuracy with the precision of 0.84 and the recall of 0.93.

According to experimental example 2, using Efficient Net B3, a spectrogram having a period of 0.5 s was used as input data, and cough/non-cough markers assessed by a person after listening to a recorded sound were applied as output data. Regarding the input data, one spectrogram was divided by frequency section and the divided spectrogram was input to a total of 512 input nodes separately. Before input to the model, the spectrogram was subjected to resizing to a size of 300*300, scaling with division by a maximum value, and gray-to-RGB conversion. A total of 350,000 pieces of training data were used to train the cough determination model, and the cough determination model showed accuracy with the precision of 0.92 and the recall of 0.9.

In general, Efficient Net B5 is known to be more accurate, but in actual experiments, it was found that Efficient Net B3 had better precision. Accordingly, it was found that in realizing a cough count model, the selection of a model size according to a data size may affect accuracy.

Referring back to FIG. 3, the server 2000 may calculate the total number of coughs in step S4000. The server 2000 may calculate the total number of coughs in the sound signal on the basis of a determination result obtained in step S3000 for a spectrogram of at least one onset signal.

According to an embodiment of the present application, steps S2000 and S3000 may be performed on each of the extracted one or more onset signals. Steps S2000 and S3000 may be performed as many times as the number of onset signals obtained in step S1000.

The server 2000 may determine the total number of coughs on the basis of the onset signals determined as coughs in step S3000. The server 2000 may determine the total number of coughs by counting the onset signals determined as coughs.

Since a cough is accompanied by a sudden change in sound pressure, a cough period in the entire sound signal may be captured by determining an onset point and extracting an onset signal. Accordingly, a cough period is captured and applied to the cough determination model, and this operation may be performed to reduce the amount of operation.

However, in this case, 1) there is an overlapping region in the time domain between two consecutive sampling sections in a general algorithm used for detection of an onset point, and 2) a cough sound has a characteristic that two or more onset points may be detected from one cough, so postprocessing needs to be performed to count coughs accurately.

According to an embodiment of the present application, the server 2000 may be realized to count one when the time interval between the time points of two adjacent onset signals determined as coughs is within a reference time interval (for example, 0.5 s).

Figure 7:
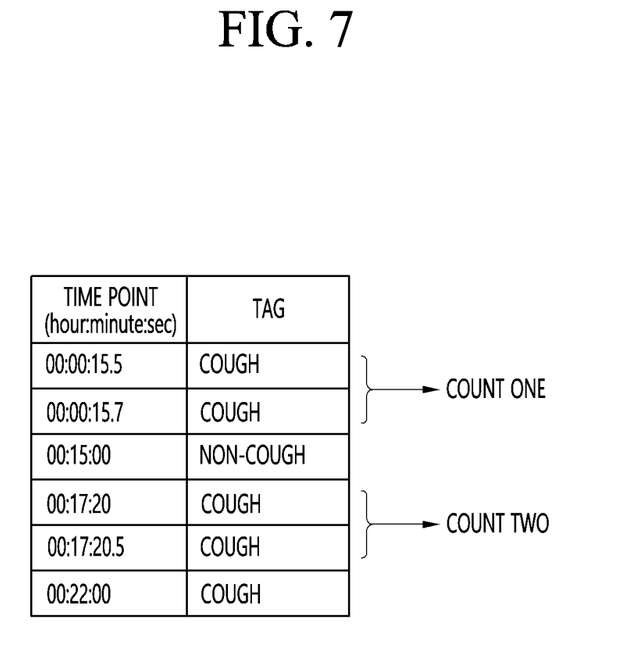
FIG. 7 is a view showing a method for counting coughs according to an embodiment of the present application.

FIG. 7 is a view showing a method for counting coughs according to an embodiment of the present application.

Referring to FIG. 7, the left column "time point" refers to a time value of the time point of an onset signal in a sound signal. In other words, when an onset point is detected 15.5 seconds after the start of a sound signal, the time point of the onset signal may be expressed as 00:00:15.5.

The right column "tag" refers to a result value determined by the cough determination model on the basis of an onset signal. In other words, when an onset signal is input to the cough determination model and is classified (or estimated) as a cough, the tag of the onset signal may be expressed as "cough".

The server 2000 may count one cough when the time interval between the time points of two adjacent onset signals is within a reference time interval. That is, with a first onset signal (00:00:15.5) determined as a cough, a second onset signal (00:00:15.7) determined as a cough, a third onset signal (00:17:20) determined as a cough, a fourth onset signal (00:17:20.5) determined as a cough, and a fifth onset signal (00:22:00) determined as a cough, the server 2000 may count one cough when the time point of the first onset signal and the time point of the second onset signal are spaced apart by 0.2 secs which is shorter than a reference time interval (0.25 secs). The server 2000 may count two coughs when the time point of the third onset signal and the time point of the fourth onset signal are spaced apart by 0.5 secs which is longer than the reference time interval (0.25 secs).

According to an embodiment of the present application, the server 2000 may not obtain the time interval between the time point of the second onset signal and the time point of the third onset signal. In other words, in the case in which one is counted when the time interval between the time point of the former onset signal and the time point of the latter onset signal is within a reference time interval, this is actually similar to "deleting" the latter onset signal, and thus the server 2000 may not compare the time point of the latter onset signal and the time point of the onset signal following the latter onset signal. Accordingly, the server 2000 may not obtain the time interval between the time point of the second onset signal and the time point of the third onset signal, and may compare the time point of the third onset signal and that of the fourth onset signal to continue the cough counting process.

According to an embodiment of the present application, the reference time interval may be shorter than 0.5 secs. This is because it is rare that a person coughs twice within 0.5 secs. Thus, according to an embodiment of the present application, the reference time interval may be set to 0.25 secs, and without being limited thereto, if necessary (for example, when the characteristic of a continuous cough is considered), an adjusted value may be used accordingly. According to an embodiment of the present application, the onset length may be longer than 0.5 secs. This is because people give most coughs within 0.5 secs, so 0.5 secs are long enough to determine whether there is a cough or not. Thus, according to an embodiment of the present application, the onset length may be set to 0.5 secs, and without being limited thereto, if necessary (for example, when a type of a cough is determined), an adjusted value may be used accordingly. The length (that is, the onset length) of an onset signal in the time domain may be longer than the reference time interval.

The embodiments according to the present disclosure described above may be realized in the form of a program instruction executable through various computer elements. Thus, the resulting program instruction may be recorded on a non-transitory computer-readable recording medium. The non-transitory computer-readable recording medium may include a program instruction, a data file, a data structure, and the like, independently or in combination. The program instruction recorded on the non-transitory computer-readable recording medium is specially designed and configured for the present disclosure, or is known to a person skilled in the art of computer software and thus is available for use. Examples of the non-transitory computer-readable recording medium include magnetic media such as hard disks, floppy disks, and magnetic tapes; optical data storage media such as CD-ROMs and DVDs; magneto-optical media such as floptical disks; and hardware devices, such as ROM, RAM, and flash memory devices, which are particularly configured to store and execute program instructions. Examples of the program instruction include machine language codes, such as ones generated by a compiler, and high-level language codes executable by a computer using an interpreter and the like. The hardware device may be configured in such a manner as to operate as one or more software modules in order to perform the operation according to the present disclosure, and vice versa.

Although the present disclosure is described with reference to specific items, such as specific elements, and some embodiments and drawings, such specific details disclosed herein are merely representative for purposes of helping more comprehensive understanding of the present disclosure. The present disclosure, however, is not limited to only the exemplary embodiments set forth herein, and those skilled in the art will appreciate that various modifications and variations may be made from the description.

Therefore, the spirit of the present disclosure shall not be limited to the above-described embodiments, and the entire scope of the appended claims and their equivalents will fall within the scope and spirit of the disclosure.

MODE FOR INVENTION

As described above, related matters have been described in Best Mode.

What is claimed is:

1. A method for counting coughs by analyzing a sound signal, the method comprising:
transforming the sound signal into an entire spectrogram image;
detecting a plurality of onset points in the entire spectrogram image,
extracting a plurality of cropped spectrogram images from the entire spectrogram image by cropping portions of the entire spectrogram image, wherein each of the cropped portions corresponds to a spectrogram image with a predetermined time length from each of the detected onset points in the entire spectrogram image;
obtaining a plurality of time points, each of the time points corresponding to a time value of the onset point of each of the plurality of cropped spectrogram images measured from a starting point of the entire spectrogram image, wherein the onset point is a starting point of corresponding cropped spectrogram image;
determining whether each of the plurality of cropped spectrogram images represents a cough by inputting each of the plurality of cropped spectrogram images into a cough determination model, wherein the cough determination model is a classification model trained to classify the inputted spectrogram image into a cough or non-cough;
determining a plurality of tags according to results determined by the cough determination model, wherein each of the plurality of tags corresponds to each of the plurality of time points, wherein the tag indicates one of the cough and non-cough; and
calculating a total number of coughs included in the sound signal based on the plurality of time points and corresponding tags,
wherein the calculating the total number of coughs comprises:
checking the plurality of tags corresponding to the time points in order of the time points,
counting one cough when the tag corresponding to the time point indicates the cough, and
not counting cough when the tag corresponding to the time point indicates the non-cough, and
wherein when a time interval between a first time point at which a corresponding tag indicates the cough and a second time point which is later in order than the first time point and at which a corresponding tag indicates the cough is within a reference time interval, the cough corresponding to the second time point is not counted towards the total number of coughs included in the sound signal and checking starts from the tag corresponding to a third time point which is later in order than the second time point.

2. The method of claim 1, wherein there's no time point at which a corresponding tag indicates the cough between the first time point and the second time point.

3. The method of claim 2, wherein there's no time point between the second time point and the third time point.

4. The method of claim 1, wherein the predetermined time length is longer than the reference time interval.

5. The method of claim 1, wherein the transforming the sound signal into the entire spectrogram image comprises:

transforming the sound signal into the entire spectrogram image by Fourier transforming the sound signal in a frequency domain.

6. The method of claim 1, wherein the determining whether each of the plurality of cropped spectrogram images represents the cough comprises:

performing at least one preprocessing of resizing, scaling and RGB conversion on the cropped spectrogram image; and determining whether the cropped spectrogram image represents the cough by inputting the preprocessed cropped spectrogram image into the cough determination model.

7. The method of claim 1, wherein the spectrogram image has the predetermined time length in a time domain.

8. The method of claim 7, wherein the cough determination model is trained using a training dataset comprising a plurality of the spectrogram image and tagging information labeled on each of the plurality of the spectrogram image, wherein the tagging information comprises information on whether the spectrogram image represents a sound corresponding to a cough.

9. The method of claim 1, wherein detecting the plurality of onset points in the entire spectrogram image comprises sampling the entire spectrogram image every predetermined sampling time and determining whether there is an onset point in corresponding predetermined sampling time.

10. The method of claim 9, wherein the predetermined sampling time is about 0.01 second.

11. The method of claim 1, wherein the method is performed by one of a smart glasses, a smart watch, a smart band, a smart ring, or a smart necklace.

12. A non-transitory computer-readable recording medium storing a computer program for executing the method of claim 1.

* * * * *